US008697677B2

(12) United States Patent
Frenneaux (10) Patent No.: US 8,697,677 B2
(45) Date of Patent: *Apr. 15, 2014

(54) PERHEXILINE FOR TREATING CHRONIC HEART FAILURE

(71) Applicant: Heart Metabolics Limited, London (GB)

(72) Inventor: Michael Paul Frenneaux, Aberdeenshire (GB)

(73) Assignee: Heart Metabolics Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/841,465

(22) Filed: Mar. 15, 2013

(65) Prior Publication Data

US 2013/0224118 A1 Aug. 29, 2013

Related U.S. Application Data

(63) Continuation of application No. 13/244,103, filed on Sep. 23, 2011, now Pat. No. 8,470,806, which is a continuation of application No. 10/592,250, filed as application No. PCT/GB2004/003835 on Sep. 7, 2004, now abandoned.

(30) Foreign Application Priority Data

Mar. 10, 2004 (GB) .................................. 0405381.5

(51) Int. Cl.
*A61K 31/56* (2006.01)
*A61K 31/415* (2006.01)

(52) U.S. Cl.
USPC .......................... 514/171; 514/406; 514/223.5

(58) Field of Classification Search
USPC ....................................... 514/171, 406, 223.5
See application file for complete search history.

(56) References Cited

U.S. PATENT DOCUMENTS

| | | | |
|---|---|---|---|
| 2003/0162824 | A1 | 8/2003 | Krul |
| 2005/0203072 | A1 | 9/2005 | Rudolph et al. |
| 2007/0275997 | A1 | 11/2007 | Frenneaux |
| 2010/0331364 | A1 | 12/2010 | Ashrafian et al. |
| 2012/0122925 | A1 | 5/2012 | Ashrafian |

FOREIGN PATENT DOCUMENTS

| | | |
|---|---|---|
| WO | 97/00678 | 1/1997 |
| WO | 2005/087233 | 9/2005 |
| WO | 2005/097121 | 10/2005 |
| WO | 2009/066085 | 5/2009 |
| WO | 2010/131033 | 11/2010 |
| WO | 2010/133815 | 11/2010 |

OTHER PUBLICATIONS

Horowitz et al. (International J. Cardiology; 13(2) 1986; 219-229 (Abstract).*
Jerant et al. (Medical Care; 39(11) 1234-1245).*
Drexler (Annu. Rev. Med. 1996. 47:241-56).*
Guidelines for Management . . . (Med J. Aust (2001);174; (9) 459-466).*
Abbate et al., "Recurrent angina after coronary revascularization: a clinical challenge." Eur Heart J., 28:1057-65 (2007).
Abozguia et al., "Modification of myocardial substrate use as a therapy for heart failure." Nat Clin Pract Cardiovasc Med.; 3(9):490-498 (2006).
Abozguia et al., "The heart metabolism: Pathophysiological aspects in ischaemia and heart failiure.", Curr Pharm Design, 15:827-835 (2009).
Arany et al, "Transcriptional coactivator PGC-1α controls energy state and contractile function of cardiac muscle", Cell Metabolism, 1: 259-271 (2005).
Arany et al., "Transverse aortic constriction leads to accelerated heart failure in mice lacking PPAR-γ coactivator 1α", PNAS, 103(26):10086-10091 (2006).
Ashrafian et al., "Metabolic mechanisms in heart failure",Circulation, 116:434-448 (2007).
Atherton et al., "Diastolic ventricular interaction in chronic heart failure", Lancet, 349:1720-1724 (1997).
Auricchio et al., "Clinical efficacy of cardiac resynchronization therapy using left ventricular pacing in heart failure patients stratified by severity of ventricular conduction delay", J Am Coll Cardiol, 42(12):2109-2116 (2003).
Bacharach et al., "Left ventricular peak ejection rate, filling rate and ejection fraction-frame requirements at rest and exercise: concise communication", Journal of Nuclear Medicine, 20:189-193 (1979).
Baicu et al, "Left ventricular systolic performance, function, and contractility in patients with diastolic heart failure", Circulation; 111:2306-2312 (2005).
Bhatia et al., "Outcome of heart failure with preserved ejection fraction in a population-based study",N Engl J Med, 355:260-269 (2006).
Boden et al., "Optimal medical therapy with or without PCI for stable coronary disease" N Engl J Med, 356(15):1503- 1516 (2007).
Bonnefont et al., "Carnitine palmitoyltransferases 1 and 2: biochemical, molecular and medicinal aspects", Mol Asp Med, 25:495-520 (2004).
Borlaug et al., "Impaired chronotropic and vasodilator reserves limit exercise capacity in patients with heart failure and a preserved ejection fraction", Circulation, 114:2138-2147 (2006).
Brubaker et al., "Chronotropic incompetence and its contribution to exercise intolerance in older heart failure patients", J Cardiopulm Rehabil, 26:86-89 (2006).

(Continued)

Primary Examiner — Shirley V Gembeh
(74) Attorney, Agent, or Firm — Nixon & Vanderhye P.C.

(57) ABSTRACT

Disclosed are methods for the treatment of chronic heart failure, comprising administering to an animal in need thereof an effective amount of perhexiline, or a pharmaceutically acceptable salt thereof, to treat said chronic heart failure. The chronic heart failure maybe non-ischaemic or ischaemic. Also disclosed is the use of perhexiline in the manufacture of a medicament to treat chronic heart failure, including chronic heart failure of a non-ischaemic origin and chronic heart failure of an ischaemic origin.

21 Claims, 4 Drawing Sheets

(56) References Cited

OTHER PUBLICATIONS

Bruce RA, McDonough Jr, "Stress testing in screening for cardiovascular disease", *Bull N Y Acad Med*, 5(12):1288-1305 (1969).

Buffon et al., "Widespread coronary inflammation in unstable angina" *N Engl J Med*, 347(1):5-12 (2002).

Burkhoff et al., "Heart failure with a normal ejection fraction: is it really a disorder of diastolic function?", *Circulation*, 107:656-658 (2003).

Cavassila et al, "Cramer-Rao bounds: an evaluation tool for quantitation", *NMR Biomed*, 14:278-283 (2001).

Chatterjee et al., "Systolic and Diastolic Heart Failure: Differences and Similarities", *Journal of Cardiac Failure*, 13(7):569-576 (2007).

Chen et al., "Noninvasive single-beat determination of left ventricular end-systolic elastance in humans", *J Am Coll Cardiol*, 38:2028-2034 (2001).

Chirkov, YY, Horowitz JD, "Impaired tissue responsiveness to organic nitrates and nitric oxide: a new therapeutic fronteer?", *Pharmacology & Therapeutics*, 116:287-305 (2007).

Cicoira et al., "Long-term, dose-dependent effects of spironolactone on left ventricular function and exercise tolerance in patients with chronic heart failure", *J Am Coll Cardiol*, 40(2):304-310 (2002).

Coats et al., "Current management of 1-8 hypertrophic cardiomyopathy", *Current Treatment Options in Cardiovascular Medicine*, 10:496-504 (2008).

Cohn, J., "The Management of Chronic Heart Failure", *New England Journal of Medicine*, 335(7):490-498(1996).

Cole et al., "Efficacy and safety of perhexiline maleate in refractory angina. A double-blind placebo-controlled clinical trial of a novel antianginal agent", *Circulation*, 81:1260-1270 (1990).

Cooper et al., "Studies on the metabolism of perhexiline in man", *Eur J Clin Pharmacol*, 32:569-576 (1987).

Cooper et al., "Polymorphic hydroxylation of perhexiline maleate in man", *J Med Genetics*, 21:27-33 (1984).

Czerwinski et al. "A controlled study of the diuretic and natriuretic of perhexiline maleate in normal human volunteers", *Postgraduate Medical Journal*, (Apr. Suppl.): 26-31 (1973).

Davies et al., "CYP2B6, CYP2D6, and CYP3A4 catalyze the primary oxidative metabolism of perhexiline enantiomers by human liver microsomes", *Drug Metab Dispos*, 35(1):128-138 (2007).

Davies et al, "Determination of the 4-monohydroxy metabolites of perhexiline in human plasma, urine and liver microsomes by liquid chromatography," *Journal of Chromatography B*, 843:302-309 (2006).

Davies et al., "Enantioselective assay for the determination of perhexiline enantiomers in human plasma by liquid chromatography", *Journal of Chromatography B*, 832: 114-120 (2006).

Davies et al., "Steady-state pharmacokinetics of the enantiomers of perhexiline in CYP2D6 poor and extensive metabolizers administered rac-perhexiline," *Br J Clin Pharmacol*, 65(3):347-354 (2008).

Davies NJ and Denison DM, "The measurement of metabolic gas exchange and minute volume by mass spectrometry alone", *Respiration Physiology*, 36(2):261-267 (1979).

Depre et al., "Glucose for the Heart", *Circulation*, 99:578-588 (1999).

Deschamps et al., "Inhibition by perhexiline of oxidative phosphorylation and the β-oxidation of fatty acids: possible role in pseudoalcoholic liver lesions", *Hepatology*, 19: 948-61 (1994).

Eckberg et al., "Defective cardiac parasympathetic control in patients with heart disease", *N Engl J Med*, 285(16):877-883 (1971).

Fardeau et al., "Muscle and nerve changes induced by perhexiline maleate in man and mice", *Muscle & Nerve*, 2:24-36 (1979).

Folmes et al., "High rates of residual fatty acid oxidation during mild ischaemia decrease cardiac work and efficiency",*J Mol Cell Cardiol*, 47:142-148 (2009).

Fragasso et al., "Effects of metabolic modulation by trimetazidine on left ventricular function and phosphocreatine/adenosine triphosphate ratio in patients with heart failure", *Eur Heart J*, 27:942-948 (2006).

Frenneaux, M, "New tricks for an old drug", *European Heart Journal*, 23:1898-1899 (2002).

Fromenty B, Pessayere D, "Inhibition of mitochondrial beta-oxidation as a mechanism of hepatotoxicity", *Pharmac Ther*; 67(1):101-154 (1995).

Fukuda et al., "Phosphorylation of Titin Modulates Passive Stiffness of Cardiac Muscle in a Titin Isoform-dependent manner", *J Gen Physiol*, 125:257-271 (2005).

Furst W and Hallstrom S, "Simultaneous determination of myocardial nucleotides, nucleosides, purine bases and creatine phosphate by ion-pair high-performance liquid chromatography", *J Chromatogr B*, 578: 39-44 (1992).

Gillebert et al., "Relaxation-systolic pressure relation: A load-independent assessment of left ventricular contractility", *Circulation*, 95:745-752 (1997).

Grossman et al., "Contractile state of the left ventricle in man as evaluated from end-systolic pressure-volume relations", *Circulation*, 56:845-852 (1977).

Heusch G., "Hibernating myocardium", *Physiol Rev*, 78(4):1055-1085 (1998).

Higginbotham et al., "Regulation of stroke volume during submaximal and maximal upright exercise in normal man", *Circ Res*, 58:281-291 (1986).

Holden K R, "Chronic Heart Failure and Disability" [Online] Aug. 7, 2007, *Disability Doc-Examining Social Security Disability*, Retrieved from the Internet: URL:http://www.disabilitydoc.com/chronic-heart~failure-and-disa/> (2007).

Horowitz et al., "Perhexiline maleate treatment for severe angina pectoris—correlations with pharmacokinetics", *Int J Cardiol*, 13:219-229 (1986).

Hulsmann et al., "Long-term effect of atenolol on ejection fraction, symptoms, and exercise variables in patients with advanced left ventricular dysfunction", *J Heart Lung Transplant*, 20:1174-1180 (2001).

Hunt et al., "ACC/AHA 2005 Guideline Update for the Diagnosis and Management of Chronic Heart Failure in the Adult: A report of the American College of Cardiology/American Heart Association Task Force on Practice Guidelines (Writing Committee to Update the 2001 Guidelines for the Evaluation and Management of Heart Failure): Developed in collaboration with the American College of Chest Physicians and the International Society for Heart and Lung Transplantation: Endorsed by the Heart Rhythm Society", *Circulation*, 112:e154-e235 available at www.acc.org (2005).

Inglis et al., "Effect of CYP2D6 metabolizer status on the disposition of the (+) and (−) enantiomers of perhexiline in patients with myocardial ischaemia", *Pharmacogenetics Genomics*, 17:305-312 (2007).

Ingwall JS and Weiss RG, "Is the failing heart energy starved?: On using chemical energy to support cardiac function", *Circulation Research*, 95:135-145 (2004).

Irvine et al., "Nitroxyl (HNO): The Cinderella of the nitric oxide story", *Trends in Pharmacol Sci*, 29(12):601-608 (2008).

Jeffrey et al, "Direct evidence that perhexiline modifies myocardial substrate utilization from fatty acids to lactate", *J Cardiovasc Pharmacol*, 25:469-472 (1995).

Kannel WB, "Incidence and epidemiology of heart failure", *Heart Failure Rev*, 5:167-173 (2000).

Kawaguchi et al., "Combined ventricular systolic and arterial stiffening in patients with heart failure and preserved ejection fraction: Implications for systolic and diastolic reserve limitations", *Circulation*, 107:714-720 (2003).

Kennedy et al., "Effect of the anti-anginal agent, perhexiline, on neutrophil, valvular and vascular superoxide formation", *Eur J Pharmacol*, 531:13-19 (2006).

Kennedy et al., "Inhibition of carnitine palmitoyltransferase-1 in rat heart and liver by perhexiline and amiodarone", *Biochem Pharmacol*, 52:273-280 (1996).

Kennedy et al., "Effect of perhexiline and oxfenicine on myocardial function and metabolism during low-flow ischemia/reperfusion in the isolated rat heart", *J Cardiovasc Pharmacol*, 36(6):794-801 (2000).

Killalea SM and Krum H, "Systematic review of the efficacy and safety of perhexiline in the treatment of ischemic heart disease", *Am J Cardiovasc Drugs*, 1(3):193-204 (2001).

(56) References Cited

OTHER PUBLICATIONS

Kiriazis H and Kranias EG, "Genetically engineered models with alterations in cardiac membrane calcium-handling proteins", *Annu Rev Physiol*, 62:321-351 (2000).
Kitakaze, Masashi et al., "New role of adenosine for the treatment of ischemic heart disease", *Journal of Clinical and Experimental Medicine*(Igaku No Ayumi), 192(1):35-39 (2000).
Lamb et al., "Diastolic dysfunction in hypertensive heart disease is associated with altered myocardial metabolism", *Circulation*, 99:2261-2267. (1999).
Lang et al., "Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology", *J Am Soc Echocardiogr*, 18:1440-1463 (2005).
Lee et al., "Metabolic manipulation of ischaemic heart disease, a novel approach to treatment", *Eur Heart J*, 25:634-641 (2004).
Lee et al., "Augmentation of Glucose Metabolism With Perhexiline Improves Maximal Oxygen Consumption and Quality of Life in Patients With Nonischaemic Dilated Cardiomyopathy", *Journal of the American College of Cardiology*, 43(5): 190-A-1088-122(2004).
Lee et al., "Metabolic modulation with perhexiline in chronic heart failure: A randomized, controlled trial of short-term use of a novel treatment", *Circulation*, 112:3280-3288 (2005).
Leite-Moreira et al., "Afterload induced changes in myocardial relaxation: A mechanism for diastolic dysfunction", *Cardiovasc Res*, 43:344-353 (1999).
Lele et al., "Determinants of exercise capacity in patients with coronary artery disease and mild to moderate systolic dysfunction. Role of heart rate and diastolic filling abnormalities", *Eur Heart J*, 17(2):204-212 (1996).
Lele et al., "Exercise capacity in hypertrophic cardiomyopathy. Role of stroke volume limitation, heart rate, and diastolic filling characteristics", *Circulation*, 92:2886-2894 (1995).
Liberts et al., "Effects of perhexiline and nitroglycerin on vascular, neutrophil and platelet function in patients with stable angina pectoris", *Eur J Pharmacol*, 560: 49-55 (2007).
Lindahl et al., "Markers of myocardial damage and inflammation in relation to long-term mortality in unstable coronary artery disease", *N Engl J Med*, 343: 1139-1147 (2000).
Lopaschuk et al., "An imbalance between glycolysis and glucose oxidation is a possible explanation for the detrimental effects of high levels of fatty acids during aerobic reperfusion of ischemic hearts", *J Pharmacol Exp Ther*, 264(1):135-144 (1993).
Magorien et al., "Hemodynamic correlates for timing intervals, ejection rate and filling rate derived from the radionuclide angiographic volume curve", *Am J Cardiol*, 53:567-571 (1984).
Mann, DL, "Mechanisms and Models in Heart Failure: A Combinatorial Approach", *Circulation*, 100:999-1008 (1999).
Mannheimer et al., "The problem of chronicrefractory angina", *Eur Heart J*, 23: 355-370 (2002).
Mantero et al., "Left ventricular diastolic parameters in 288 normal subjects from 20 to 80 years old", *Eur Heart J*, 16:94-105 (1995).
Metra et al., "Treatment of advanced chronic heart failure with normal left ventricular ejection fraction. Response to the letter by Dr. Martinez-Selles", *European Journal of Heart Failure*, 9(12)1224-1225 (2007).
Metra et al., "Advanced chronic heart failure: A position statement from the Study Group on Advanced Heart Failure of the Heart Failure Association of the European Society of Cardiology", *European Journal of Heart Failure*, 9:684-694 (2007).
Morgan et al., "Impaired oxidation of debrisoquine in patients with perhexiline liver injury", *Gut*, 25: 1057-1064 (1984).
Murnaghan MF, "Effect of fatty acids on the ventricular arrhythmia threshold in the isolated heart of the rabbit", *Br J Pharmacol*, 73(4):909-915 (1981).
Najjar et al., "Age and gender affect ventricular-vascular coupling during aerobic exercise", *J Am Coll Cardiol*, 44:611-617 (2004).

Naressi et al., "Java-based graphical user interface for MRUI, a software package for quantitation of in vivo/medical magnetic resonance spectroscopy signals", *Comput Biol Med*, 31(4):269-286 (2001).
Neubauer et al., "Myocardial phosphocreatine-to-ATP ratio is a predictor of mortality in patients with dilated cardiomyopathy", *Circulation*, 96:2190-2196 (1997).
Neubauer et al., "Contributions of 31P-magnetic resonance spectroscopy to the understanding of dilated heart muscle disease", *Eur Heart J*, 16(Suppl O):115-118 (1995).
Neubauer et al., "31P magnetic resonance spectroscopy in dilated cardiomyopathy and coronary artery disease. Altered cardiac high-energy phosphate metabolism in heart failure", *Circulation*, 86(6):1810-1818 (1992).
Neubauer S, "The failing heart—an engine out of fuel", *N Engl J Med*, 356: 1140-1151 (2007).
Nihoyannopoulos et al., "Diastolic function in hypertrophic cardiomyopathy: relation to exercise capacity", *J Am Coll Cardiol*, 19:536-540 (1992).
O'Brien et al., "Cardiac troponin I is a sensitive, specific biomarker of cardiac injury in laboratory animals", *Laboratory Animals*; 40:153-171 (2006).
Ommen et al., "Clinical utility of Doppler echocardiography and tissue Doppler imaging in the estimation of left ventricular filling pressures: A comparative simultaneous Dopplercatheterization study", *Circulation*, 102:1788-1794 (2000).
Ordidge et al, "Separate water and fat MR images", Letters to the Editor, *Radiology*, 157(2):551-553 (1985).
Peltier et al., "Treatment practices in heart failure with preserved left ventricular ejection fraction: A prospective observational study", *International Journal of Cardiology*, 118(3):363-369 (2007).
Pena JR and Wolska BM, "Troponin I phosphorylation plays an important role in the relaxant effect of β-adrenergic stimulation in mouse hearts", *Cardiovasc Res*, 61:756-763 (2004).
Pepine et al., "Alteration of left ventricular responses to ischemia with oral perhexiline", *Postgraduate Medical Journal*, Apr. Suppl:43-46 (1973).
Pepine et al., "Effects of perhexiline on coronary hemodynamic and myocardial metabolic responses to tachycardia", *Circulation*, 49:887-893 (1974).
Perseghin et al., "Left ventricular function and energy metabolism in middle-aged men undergoing long lasting sustained aerobic oxidative training", *Heart Online*(downloaded from heart.bmj.com-Nov. 21, 2008) doi:10.1136/hrt.2008.154716 (published online Nov. 13, 2008).
Phan et al., "Dynamic changes in left ventricular function on exercise in heart failure with preserved ejection fraction: The role of myocardial energy deficiency", *Heart*, 95:114 (2009).
Phan et al., "Heart Failure With Preserved Ejection Fraction is Characterized by Dynamic Impairment of Active Relaxation and Contraction of the Left Ventricle on Exercise and Associated With Myocardial Energy Deficiency", *J. Am. Coll. Cardiol.*, 54:402-409 (2009).
Porrello et al, "Heritable pathologic cardiac hypertrophy in adulthood is preceded by neonatal cardiac growth restriction", *Am J Physiol Regul Integr Comp Physiol*, 296:R672-R680 (2009).
Poupon et al., "Perhexiline maleate-associated hepatic injury prevalence and characteristics", *Digestion*, 20: 145-150 (1980).
Ritchie et al., "Exploiting cGMP-based therapies for the prevention of left ventricular hypertrophy: NO & beyond", *Pharmacol Ther*, 124:279-300 (2009).
Ritchie et al., "B-type Natriuretic Peptide: Endogenous regulator of myocardial structure, biomarker and therapeutic target", *Curr Mol Med*, 9:814-25 (2009).
Robertson et al., "The effect of troponin I phosphorylation on the $Ca^{2+}$-binding properties of the $Ca^{2+}$-regulatory site of bovine cardiac troponin", *J Biol Chem*, 257(1):260-263 (1982).
Rossi et al., "Chronic heart failure with preserved left ventricular ejection fraction: Diagnostic and prognostic value of left atrial size", *International Journal of Cardiology*, 110(3):386-392 (2006).
Rupp et al, "The use of partial fatty acid oxidation inhibitors for metabolic therapy of angina pectoris and heart failure", *Herz*, 27:621-636 (2002).

(56) References Cited

OTHER PUBLICATIONS

Sallustio et al., "Pharmacokinetics of the antianginal agent perhexiline: Relationship between metabolic ratio and steady-state dose", *Br J Clin Pharmacol*, 54:107-14 (2002).
Scheuermann-Freestone et al., "Abnormal cardiac muscle function in heart failure is related to insulin resistance", *Cardiovasc J S Afr*, 15(4 Suppl 1):12, #52 (2004).
Scheuermann-Freestone et al., "Abnormal cardiac and skeletal muscle energy metabolism in patients with type 2 diabetes", *Circulation*, 107:3040-3046 (2003).
Seth et al., "Alterations in isoproterenol-induced cardiac metabolic changes by perhexiline", *Indian J Med Res*, 81:224-229 (1985).
Shinke, Toshirou, "Treatment of Heart Failure Associated With Ischemic Heart Disease", *Clinical Practice and Study*, 78(9):73-79 (2001).
Shivu et al., "31P magnetic resonance spectroscopy to measure in vivo cardiac energetics in normal myocardium and hypertrophic cardiomyopathy: Experiences at 3T", *Eur J Radiol*, 73:255-259 (2010).
Singlas et al., "Pharmacokinetics of perhexiline maleate in anginal patients with and without peripheral neuropathy", *Eur J Clin Pharmacol*, 14:195-201 (1978).
Smith et al., "Altered creatine kinase adenosine triphosphate kinetics in failing hypertrophied human myocardium", *Circulation*, 114:1151-1158 (2006).
Stanley et al., "Myocardial substrate metabolism in the normal and failing heart", *Physiol Rev*, 85:1093-129 (2005).
Stewart et al., "More 'malignant' than cancer? Five-year survival following a first admission for heart failure", *Eur J Heart Fail*, 3:315-322 (2001).
Stewart et al., "Relationship between plasma perhexiline concentration and symptomatic status during short-term perhexiline therapy", *Ther Drug Monit*, 18:635-639 (1996).
Szibor M and Holtz J, "Mitochondrial ageing", *Basic Res Cardiol*, 98:210-218 (2003).
Takei, Kumiko et al., "Three Cases of Acute Exacerbation of Chronic Heart Failure Treated With Milrinone", *Therapeutic Research*, 20(8):245-251 (1999).
Takimoto et al., "Frequency-and afterload-dependent cardiac modulation in vivo by troponin I with constitutively active protein kinase A phosphorylation sites", *Circ Res*, 94:496-504 (2004).
Teerlink et al., "Progressive ventricular remodeling in response to diffuse isoproterenol-induced myocardial necrosis in rats", *Circ Res*, 75:105-113 (1994).
Teo et al., "Perhexiline during exercise training in coronary heart disease", *Clinical Pharmacology and Therapeutics*, 34(6):744-748 (1983).
Unger et al., "Dissociation between metabolic and efficiency effects of perhexiline in normoxic rat myocardium", *J Cardiovasc Pharmacol*, 46:849-855 (2005).
Unger et al., "Perhexiline improves symptomatic status in elderly patients with severe aortic stenosis", *Aust NZ J Med*, 27:24-28 (1997).
Vasan et al., "Prevalence, clinical features and prognosis of diastolic heart failure: an epidemiologic perspective", *JACC*, 26(7):1565-1574 (1995).
Vescovo et al., "Improved exercise tolerance after losartan and enalapril in heart failure: Correlation with changes in skeletal muscle myosin heavy chain composition", *Circulation*, 98(17):1742-1749 (1998).
Westermann et al., "Role of left ventricular stiffness in heart failure with normal ejection fraction", *Circulation*, 117:2051-2060 (2008).
Willoughby et al., "Beneficial clinical effects of perhexiline in patients with stable angina pectoris and acute coronary syndromes are associated with potentiation of platelet responsiveness to nitric oxide", *Eur Heart J*, 23:1946-1954 (2002).
Willoughby et al., "Platelet nitric oxide responsiveness: A novel prognostic marker in acute coronary syndromes", *Arterioscler Thromb Vasc Biol*, 25: 2661-2666 (2005).
Wright et al., "The absorption, excretion and metabolism of perhexiline maleate by the human", *Postgrad Med J*, 49 (Apr. Suppl 3):8-15 (1973).
Yagi et al., "Sustained currents through ASIC3 ion channels at the modest pH changes that occur during myocardial ischemia", *Circ Res*, 99:501-509 (2006).
Yang et al., "Current and future treatment strategies for refractory angina", *Mayo Clin Proc*, 79(10):1284-1292 (2004).
Yu et al., "Progression of systolic abnormalities in patients with "isolated" diastolic heart failure and diastolic dysfunction", *Circulation*, 105:1195-1201 (2002).
Zanger et al., "Cytochrome P450 2D6: Overview and update on pharmacology, genetics and biochemistry", *Naunyn-Schmiedeberg's Arch Pharmacol*, 369:23-37 (2004).
Zhang et al, "Cardiac troponin I phosphorylation increases the rate of cardiac muscle relaxation", *Circ Res*, 76:1028-1035.
Zile et al., "Diastolic heart failure—abnormalities in active relaxation and passive stiffness of the left ventricle", *N Engl J Med*, 350:1953-1959 (2004).
Zile MR and Brutsaert DL, "New concepts in diastolic dysfunction and diastolic heart failure: Part I: Diagnosis, prognosis, and measurements of diastolic function", *Circulation*, 105:1387-1393 (2002).
Notification of Reasons for Refusal issued in JP 2007-502376, (with English translation) Jan. 12, 2011.
Butera et al., "Heart Rate Variability in Children With Hypertrophic Cardiomyopathy", *Heart*, 89:205-206 (2003).
Maron et al., "Usefulness of B-Type Natriuretic Peptide Assay in the Assessment of Symptomatic State in Hypertrophic Cardiomyopathy:", *Circulation*, 109:984-989 (2004).
Hunt et al., 'ACC/AHA Guidelines for the Evaluation and Management of Chronic Heart Failure in the Adult: Executive Summary a Report of the American College of Cardiology/American Heart Association Task Force on Practice Guidelines (Committee to Revise the 1995 Guidelines for the Evaluation and Management of Heart Failure) *Circulation*, 104:2996-3007 (2001).
Sasson et al., "Causal Relation Between the Pressure Gradient and Left Ventricular Ejection Time in Hypertrophic Cardiomyopathy," *JACC*, 13:1275-1279 (1989).
Gould et al., "Stereoselective pharmacokinetics of perhexiline," *Xenobiotica*, 16(5):491-502 (1986).
Ashrafian et al., "Perhexiline," *Cardiovascular Drug Reviews*, 25(2):76-97 (2007).
Williams et al., "Syncope in hypertrophic cardiomyopathy: Mechanisms and consequences for treatment," *Europace*, 9:817-822 (2007).
De Keulenaer et al., "Systolic and diastolic heart failure: Different phenotypes of the same disease?" *European Journal of Heart Failure*, 9:136-143 (2007).

\* cited by examiner

FIG. 1

$^{31}$P MRS spectra of right calf muscle at rest, during and after exercise. PCr = phosphocreatine, Pi = inorganic phosphate, γ, α, β = the three phosphate groups of Adenosine Triphosphate.

Primary and selected secondary endpoints. (All P values refer to ANCOVA of the differential effect of perhexiline vs. placebo)

FIG. 3

†† p = 0.07, §§ p = 0.03, ‖ p = 0.04, # p = 0.02
Tissue Doppler endpoints. (All P values refer to ANCOVA of the differential effect of perhexiline vs. placebo)

FIG. 4

PERHEXILINE FOR TREATING CHRONIC HEART FAILURE

CROSS-REFERENCE TO RELATED APPLICATIONS

This application is a continuation of U.S. application Ser. No. 13/244,103, filed Sep. 23, 2011, which is a continuation of U.S. application Ser. No. 10/592,250, filed on Sep. 8, 2006, (and afforded a 35 U.S.C. 371(c)(1), (c)(2), and (c)(4) requirements date of receipt of Jul. 2, 2007), which is the National Stage of International Application No. PCT/GB2004/003835, filed Sep. 7, 2004, which claims the benefit of GB 0405381.5, filed Mar. 10, 2004. The entire contents of each of the above-identified applications are incorporated herein by reference.

BACKGROUND OF THE INVENTION

Chronic heart failure (CHF) is associated with considerable morbidity and mortality despite recent advances in heart treatments. There are a number of aetiological conditions that ultimately result in chronic heart failure including coronary artery disease, different cardiomyopathies, hypertension, or valvular diseases. A detailed characterization of chronic heart failure as a clinical syndrome may be found in Hunt S A, Baker D W, Chin M H, Cinquegrani M P, Feldman A M, Francis G S, Ganiats T G, Goldstein S, Gregoratos G, Jessup M L, Noble R J, Packer M, Silver M A, Stevenson L W. ACC/AHA guidelines for the evaluation and management of chronic heart failure in the adult: a report of the American College of Cardiology/American Heart Association Task Force on Practice Guidelines (Committee to Revise the 1995 Guidelines for the Evaluation and Management of Heart Failure). 2001. American College of Cardiology (http://www.acc.org/clinical/guidelines/failure/hf_index.htm).

Coronary artery disease (obstruction or blockage of the arteries of the heart) leads to ischaemia; this is characterized by a lack of blood supply to tissues; in this case the heart. This lack of this essential oxygen and nutrients can result in the tissue becoming impaired or permanently damaged. Once damaged the cardiac tissue is unable to perform its function. As such, the strength and efficiency of the heart muscle is reduced (this is technically termed left ventricular systolic dysfunction and results in a reduced ejection fraction; a measure of the pumping capacity of the heart). In addition to its ability to damage the heart muscle; cardiac ischaemia is frequently though not invariably identified by the physical symptom of angina (in some cases—ischaemia may occur without the correlate of anginal chest pain). Angina typically occurs under circumstances that would be expected to increase the hearts workload; resulting in an increased requirement for energy. This increased energy requirement necessitates increased oxygen provision that cannot be provided in the presence of arterial blockage; causing relative ischaemia and hence pain. Exercise is a good example of this, where the output of the heart is increased but the blood supply does not match this increase in performance and thus some of the heart tissue becomes ischaemic resulting in pain. This ischaemia, despite causing pain need not invariably result in irreversible heart damage and is not invariably related to pump dysfunction. Although ischaemia can cause both angina and heart failure, the exact manifestation of ischaemia relates to its severity and time course. Ultimately ischaemia as an inciting influence for heart failure is dissociable from its capacity to cause angina; they may or may not co-exist.

However, a lack of blood supply is only one of the many causes for cardiac pump impairment. Other reasons include cardiac arrhythmias (abnormal heart electrical rhythms), hypertension (high blood pressure), valve diseases, infections, toxins or impairment in the nervous stimulation of the heart to name but a few.

While these initial insults to the heart are diverse in character and severity, their common feature is that they cause either damage to heart muscle cells (myocytes) or at least impair their ability to contract. This results in left ventricular systolic dysfunction. It is this common feature that triggers the cascade that results in the stereotyped and distinct state of chronic heart failure. As discussed in "Mechanisms and Models in Heart Failure: A Combinatorial Approach", by Douglas L. Mann, MD, Circulation, 1999; pages 999-1008 and in "Drug Therapy: The Management of Chronic Heart Failure", by Jay N. Cohn, MD, New England Journal of Medicine 1996; pages 490-498), heart failure may be viewed as a progressive disorder that is initiated after an index event either damages the heart muscle, with a resultant loss 15 of functioning cardiac myocytes, or alternatively disrupts the ability of the myocardium to generate force, thereby preventing the heart from contracting normally. This index event may have an abrupt onset, as in the case of a myocardial infarction (heart attack), it may have a gradual or insidious onset, as in the case hemodynamic pressure or volume overloading, or it may be hereditary, as in the case of many of the genetic cardiomyopathies.

Regardless and irrespective of the diverse nature of the inciting event, the feature that is common to all of these index events is that they all, in some manner, produce a decline in pumping capacity of the heart. Following the initial decline in pumping capacity of the heart, acutely, patients may become very symptomatic; they may be minimally symptomatic or may even remain asymptomatic. However, the decreased pump capacity generally results in a diminished cardiac output. This chronically activates the neurohumoral system, particularly the sympathetic nervous system, the renin-angiotensin-aldosterone system, and potentiates the release of vasopressin.

Figure 1:
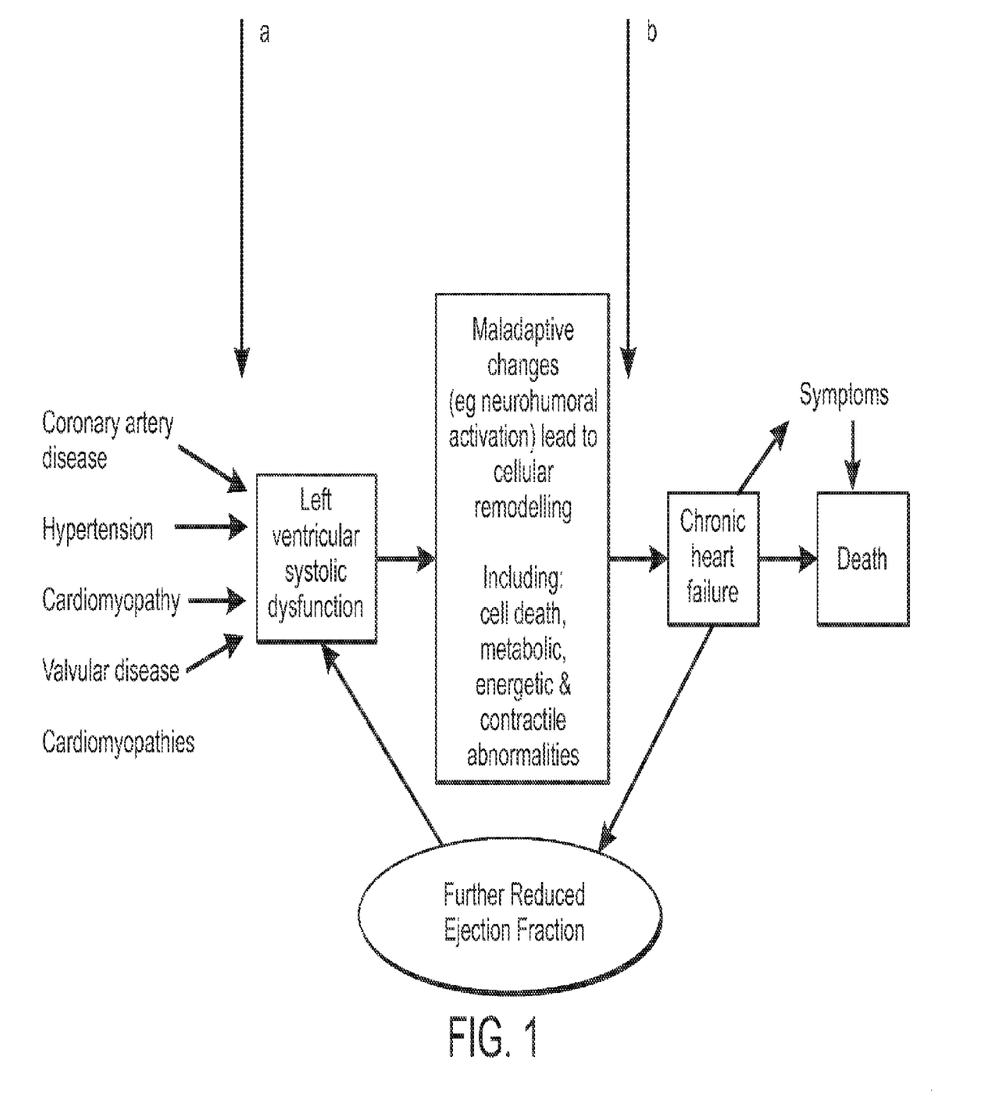
FIG. 1 shows how there is an inciting phase of heart failure.
Figure 2:
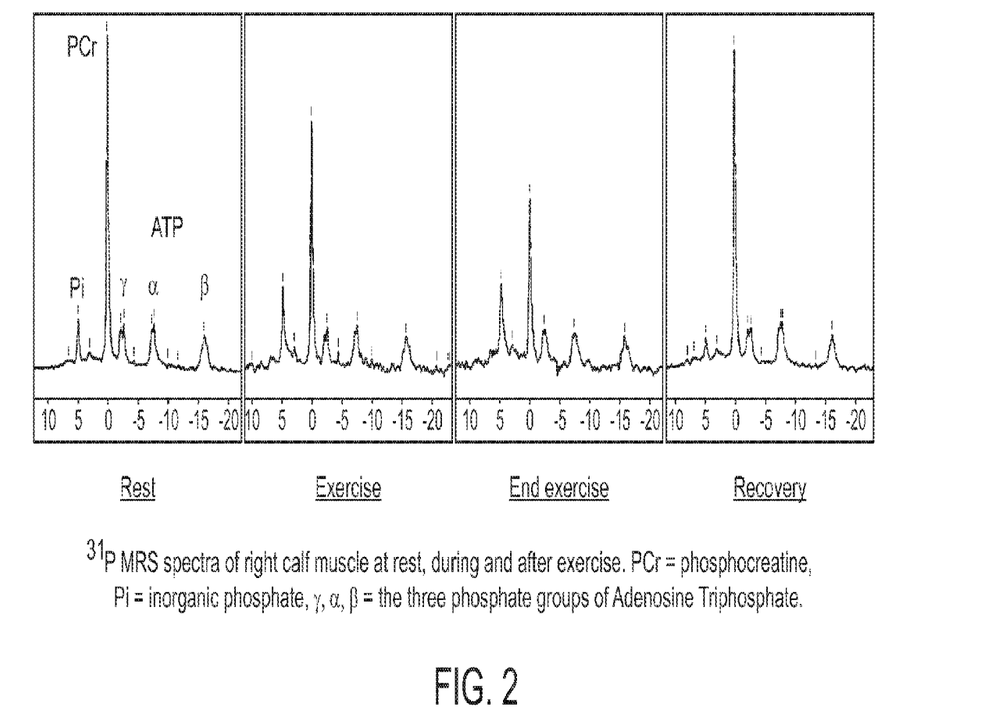
FIG. 2 shows $^{31}$P MRS spectra of a right calf muscle at rest, during and after exercise.

Although in the short term these adaptations are beneficial due to their capacity to maintain blood flow to vital organs; in the long term, these reflexes have deleterious effects and ultimately result in cardiac remodeling (FIG. 1). This remodelling is the central stereotyped feature of CHF irrespective of the inciting influence and is manifest at the macroscopic level (visible to the eye) by dilatation of the heart chambers. However there is also corresponding remodelling at the molecular and the cellular level. These include changes in cellular transcription (the genetic programmes determining cellular function) and the resulting cellular pathways. One aspect of cellular function that is altered in chronic heart failure is cellular metabolism and energy production.

The common unified programme of the failing heart irrespective of the inciting insult thus includes chronic energy starvation. It has been postulated that these energy changes are not simply just a feature of CHF but are of mechanistic importance in chronic heart failure. The failing heart is characterized by a marked change in substrate preference away from fatty acid metabolism toward glucose metabolism. Glucose is a more efficient cellular fuel and this particular adaptation may therefore be an adaptive feature of chronic heart failure—partially mitigating the effect of energy deficit. It therefore follows that augmentation of "metabolic remodeling" is a potential target in chronic heart failure; however to date there has been a paucity of even animal data to confirm this assertion.

Perhexiline (2-(2,2-dicyclohexylethyl)piperidine) is a known anti-anginal agent that operates principally by virtue of its ability to shift metabolism in the heart from free fatty acid metabolism to glucose, which is more energy efficient. Aside from being used for the treatment of angina as a manifestation of ischaemia (in patients who may or may not coincidentally have heart failure), there is no record of using perhexiline to treat instances of non-ischaemia and certainly no known use of this drug to treat instances of heart failure independent of angina. Phrased alternatively; while perhexiline has been used to treat patients with angina and ischaemia at the point where this may be an inciting influence for heart failure as demonstrated by arrow (a) in FIG. 1, (which therefore may or may not be associated with active ischaemia-related pump dysfunction or ischaemia-related congestive cardiomyopathy); there has never been a suggestion that perhexiline may be useful in the modification of chronic metabolic remodelling in the distinct stereotyped phenotype of chronic heart failure as demonstrated by arrow (b) in FIG. 1.

With further reference to FIG. 1, it is apparent that there is an inciting phase of heart failure, which is due to diverse initiating influences. While completely unrelated to one another, these diverse influences all result in pump failure and left ventricular systolic dysfunction. Irrespective of inciting influence, this pump failure initiates an initially adaptive but ultimately partially maladaptive remodelling. This chronic remodelling is a stereotyped molecular, cellular and macroscopic phenomenon, and the central cause of eventual progressive chronic heart failure. Chronic heart failure remodelling ultimately leads to a vicious cycle of detrimental events. Part of the chronic heart failure phenotype is energetic deficiency and a shift in cellular metabolism away from fatty acid metabolism to glucose metabolism.

SUMMARY OF THE INVENTION

Hitherto, perhexiline has been used as an anti-ischaemic agent at juncture a, the inciting phase; although even at this stage it has not been used explicitly as an antifailure agent. The present invention postulates that metabolic manipulation with perhexiline is effective in modifying not an inciting influence; but rather the common programme of the chronic heart failure state; hence this invention postulates a role for treating chronic heart failure at the distinct juncture b.

The present invention is thus based on the hypothesis that perhexiline-induced metabolic modification may be beneficial to treatment of the stereotyped chronic heart failure state irrespective of its effect on the inciting aetiology. The corollary of this assertion would be that if indeed the effect of perhexiline is as a metabolic modifier of CHF rather than a simple anti-ischaemic agent; its benefit in both ischaemically-induced CHF and non-ischaemically induced CHF would be similar. The invention is supported by the first clinical data to show that any metabolic modifier (perhexiline in this case) is capable of improving human chronic heart failure; furthermore the hypothesis is supported by the finding that the benefit of perhexiline in patients having ischaemic or non-ischaemic heart failure as assessed by improvements in a number of key indicators associated with chronic heart failure, was remarkably similar.

DETAILED DESCRIPTION OF THE INVENTION

According to a first aspect of the present invention, there is provided a method of treating chronic heart failure, which comprises administering to an animal in need thereof an effective amount of perhexiline, or a pharmaceutically acceptable salt thereof, to treat said chronic heart failure. The animal is preferably a mammal and most preferably a human.

In one embodiment, said chronic heart failure may be chronic heart failure as a result of an initial inciting influence of ischaemia.

In another embodiment, said chronic heart failure may be as a result of an initial nonischaemic inciting influence, that is to say, chronic heart failure in the absence of significant coronary artery disease, as for example may be determined by coronary angiography.

According to another aspect of the present invention, there is provided the use of perhexiline in the manufacture of a medicament to treat chronic heart failure. In one embodiment, the medicament is for the treatment of non-ischaemic chronic heart failure, that is chronic heart failure in the substantial absence of inciting ischaemia. In another embodiment, the medicament is for the treatment of chronic heart failure having an ischaemic inciting origin.

In aspects of the present invention, the perhexiline exists in the form of a salt of perhexiline, preferably the maleate salt. The perhexiline may be sued at doses in the normal therapeutic range for perhexiline (Kennedy J A, Kiosoglous A J, Murphy G A, Pelle M A, Horowitz J D. "Effect of perhexiline and oxfenicine on myocardial function and metabolism during low-flow ischemia/reperfusion in the isolated rat heart", J Cardiovasc Pharmacal 2000; 36(6):794-801).

Physiologically acceptable formulations, such as salts, of the compound perhexiline, may be used in the invention. Additionally, a medicament may be formulated for administration in any convenient way and the invention therefore also includes within its scope use of the medicament in a conventional manner in a mixture with one or more physiologically acceptable carriers or excipients. Preferably, the carriers should be "acceptable" in the sense of being compatible with the other ingredients of the formulation and not deleterious to the recipient thereof. The medicament may be formulated for oral, buccal, parental, intravenous or rectal administration. Additionally, or alternatively, the medicament may be formulated in a more conventional form such as a tablet, capsule, syrup, elixir or any other known oral dosage form.

According to a further aspect of the invention there is provided a treatment programme for treating chronic heart failure, which involves the co-use or coadministration of perhexiline with one or more other compounds that are advantageous in treating chronic heart failure or the symptoms thereof. In one embodiment, the programme is for the treatment of non-ischaemic chronic heart failure, that is chronic heart failure in the substantial absence of inciting ischaemia. In another embodiment, the programme is for the treatment of chronic heart failure having an ischaemic inciting origin.

EXAMPLE

An embodiment of the invention will now be described by way of example only wherein a double-blind, randomised, placebo-controlled study was undertaken in order to investigate the effects of perhexiline on chronic heart failure. 56 patients with CHF were recruited and all provided written informed consent. Entry criteria were as follows: left ventricular ejection fraction (LVEF) <40%, optimally medicated heart failure with New York Heart Association (NYHA) Class II-III symptoms. Cardiopulmonary exercise testing with respiratory gas analysis, completion of the Minnesota Living with Heart Failure Questionnaire. (MLHFQ) and 2-D echocardiography were performed at baseline on all patients.

Patients were then allocated to two groups (ischemic or non-ischemic) depending on the presence or absence of significant coronary artery disease during coronary angiography.

The ischemic group (n=30) was also subjected to dobutamine stress echocardiography at baseline. The non-ischemic group (n=26) was subjected to $^{31}$P magnetic resonance spectroscopy to measure changes in muscle mitochondrial function.

All Patients:
Cardiopulmonary Exercise Test

Incremental exercise testing with assessment of respiratory gas exchange was performed on a treadmill using the Weber protocol. Breath by breath respiratory gases were measured during exercise using a Pulmolab EX670 system mass spectrometer which was calibrated before every study. Raw data were averaged to 30 second intervals and oxygen consumption during peak exercise was obtained (V0$_2$max; ml/kg/min). Electrocardiograms and blood pressure were monitored throughout. Exercise was terminated at the subject's request due to fatigue or breathlessness.

Minnesota Living with Heart Failure Questionnaire (MLHFQ)

A standard 21-question MLHFQ was employed to determine if perhexiline affected patient quality of life. This is a well validated measure of symptomatology in heart failure (17) and includes questions to assess the ability to perform activities of daily living as well as questions gauging the severity of symptoms due to heart failure. Each question was scored out of 5. The sum of the scores were calculated where a higher score indicated a poorer quality of life. All patients completed the questionnaires alone and without assistance.

Resting Echocardiography

Echocardiography was performed with patients in the left lateral decubitus position using a Vingmed System V echocardiographic machine and a 2.5 MHz transducer. Images were stored digitally. Resting scans were acquired using standard echocardiographic windows for LVEF, transmitral valve Doppler, and resting tissue Doppler. Tissue Doppler echocardiography allows objective assessment of regional wall motion and is superior to conventional greyscale echocardiography when used in conjunction with dobutamine stress (18).

Left ventricular volumes for calculation of LVEF were obtained using biplane echocardiography and the modified Simpson's formula. Volumes were averaged over 3 beats. In addition, on-line tissue Doppler peak systolic velocity (PSV) of the lateral mitral valve annulus was obtained as a reflection of left ventricular long-axis function.

In theory, improving metabolic efficiency would also lead to an improvement in diastolic function of the left ventricle as energy is also required for cardiac relaxation. The ratio of peak E wave from transmitral valve Doppler vs. the E wave from tissue Doppler of the lateral mitral valve annulus (E:EA ratio) is a sensitive indicator of left ventricular end diastolic pressure (19).

Ischemic Group:

Tissue Doppler assessment of the left ventricle was performed at rest and analysed off-line using Echopac software in order to determine regional myocardial PSV from 15 left ventricular segments described in detail elsewhere (20). These segments were selected to include all areas supplied by the three major coronary arteries and for the greatest reproducibility for acquisition of PSV (21). (See FIG. 4)

Dobutamine Stress Echocardiography

Following resting echocardiography dobutamine infusion was commenced via a syringe driver and incremented at 3 minute intervals from 5 mcg/kg/min to 10, 20, 30 and 40 mcg/kg/min. Digital loops of 15 views outlined above were stored at 90 seconds of each stage. Up to 1 mg of atropine was given if the hemodynamic response was submaximal. Electrocardiograms and blood pressure were monitored at each stage. End-points for termination of the test were attainment of ≥85% of the target heart rate, evidence of ischemia, or severe side effects from dobutamine. Data from all stages were analysed off-line as with the resting images.

PSV data are expressed as velocity at rest, low dose dobutamine infusion (10 mls/kg/min) and peak dose dobutamine infusion (the last infusion stage before infusion terminated, which may include the addition of atropine).

Non-Ischemic Group:
$^{31}$P Magnetic Resonance Spectroscopy

Patients with CHF have abnormally rapid skeletal muscle phosphocreatine (a high energy phosphate metabolite critically involved in muscle contraction) depletion during exercise with delayed recovery(22). $^{31}$P magnetic resonance spectroscopy allows changes in skeletal muscle intracellular high energy phosphate compounds and pH to be measured non-invasively. At the end of exercise, because glycogenolysis has stopped and phosphocreatine resynthesis is purely oxidative, analysis of phosphocreatine recovery provides information about skeletal muscle mitochondrial function. In order to determine the effect of augmenting glucose metabolism on muscle energetics, magnetic resonance spectroscopy of calf muscle before, during and after local exercise was performed. Only patients in the nonischemic heart failure population were subjected to magnetic resonance spectroscopy as underlying peripheral vascular disease leads to abnormalities in skeletal muscle energetics independent of heart failure.

Skeletal muscle high-energy phosphate metabolism was measured using a 2-Tesla superconducting whole-body magnet interfaced to a Bruker Avance spectrometer at least 3 days after the peak exercise tolerance test. The methodology has been described in detail elsewhere (23).

Figure 3:
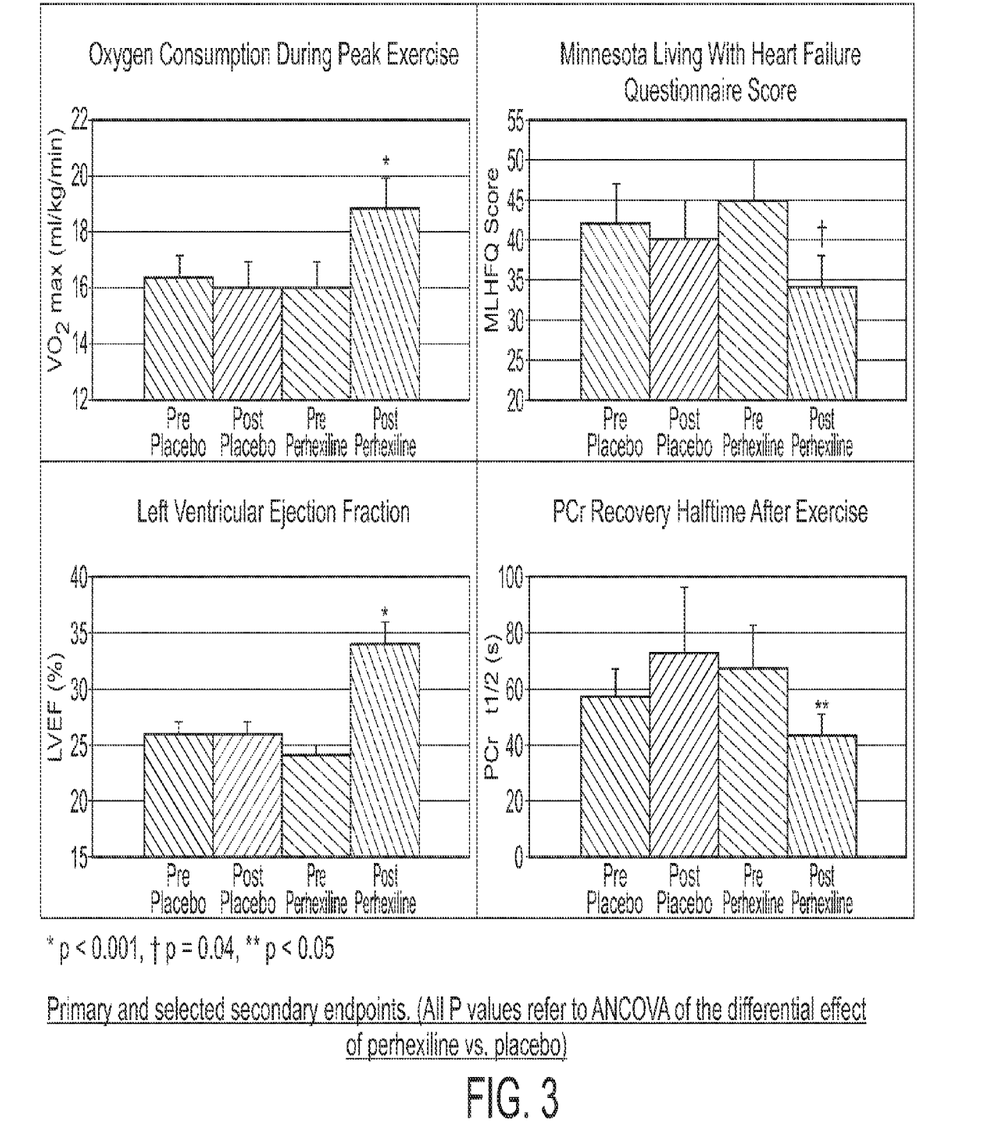
FIG. 3 shows data for primary and secondary end-points as discussed in the "Results" section.

Briefly, subjects were positioned within the magnet in the supine position with a 6 cm diameter surface coil under the maximal circumference of the right calf muscle. $^{31}$Phosphorus spectra were collected at rest, during exercise and recovery. Following spectral acquisition at rest, a standardized exercise protocol was employed which involved plantar flexion at 0.5 Hz lifting 10% of lean body mass a distance of 7 cm. This workload was continued for 4 minutes before being incremented by 2% of lean body mass for every subsequent minute until fatigue or phosphocreatine hydrolysis reached 50% of the resting level. Recovery spectra were subsequently acquired for 11 minutes. Examples of the spectra obtained during a typical study are shown in FIG. 3.

Phosphocreatine concentrations were quantified using a time-domain fitting routine (VARPRO, R. de Beer). Phosphocreatine recovery halftime following exercise (PCr t½), a marker of skeletal muscle mitochondrial function which is independent of skeletal muscle mass and exercise intensity, was calculated as previously described(24).

Intervention

Following baseline studies, patients were randomized in a double-blind fashion to receive either perhexiline (n=28) or placebo (n=28) 100 mg twice daily. Blood was obtained at 1, 4, and 8 weeks after initiation of the drug for measurements of serum perhexiline levels with subsequent dose titration in order to prevent toxicity. Dose adjustments were advised as per a standard protocol by an unblinded physician. Identical dosage adjustments were also made for randomly allocated placebo-treated patients by the unblinded observer in order to ensure blinding of the investigators was maintained. After 8 weeks of treatment, patients were re-evaluated as above.

Statistics

The primary end-point for this study was pre-defined as $VO_2$max with the following secondary endpoints: MLHFQ score, LVEF, E:EA ratio, resting, low dose and high dose mean PSV during stress echocardiography and PCr t½. Therapy randomization of the ischemic and non-ischemic groups occurred separately but with similar protocols in order to allow for pre-hoc analysis of the primary endpoint in each group. The study had a 95% power to detect a 2 ml/kg/min increase in $VO_2$max in the active vs. placebo groups with a significance level of 0.05. Data were analyzed with SPSS 11.5 for Windows© and expressed as mean ± standard error of mean. ANCOVA using baseline values as covariates was performed to test for significance of differences seen in the perhexiline vs. placebo groups following treatment. A p value of <0.05 was taken to indicate statistical significance.

Results

All patients completed the 8-week course of treatment. There were no deaths in either group during the study period. Side effects in the perhexiline group were restricted to transient nausea and dizziness during the first week of treatment (n=3).

Both groups were well matched for baseline characteristics and treatment (Table 1). There was a significant fall in the NYHA class within the perhexiline group after treatment (p=0.02).

$VO_2$max at baseline was similar in the perhexiline and placebo groups (Table 2). Following treatment, $VO_2$max was unchanged in the placebo group but markedly increased by 2.7±0.8 ml/kg/min (16.7%) in the perhexiline group. ANCOVA demonstrated a significant effect of perhexiline vs. placebo on $VO_2$max; p<0.001. The increase in $VO_2$max in the ischemic and non-ischemic group were 2.9±1.2 ml/kg/min (p=0.008) and 2.5±0.4 ml/kg/min (p=0.03) respectively. Exercise time tended to increase in the perhexiline group.

MLHFQ scores were significantly reduced by 24.4% following treatment in the perhexiline group (p=0.04) but unchanged in the placebo group. Perhexiline therapy was also associated with a significant reduction in PCr t½ (from 67±15 to 44±7 seconds; p<0.05) in the non-ischemic group. The normal range for PCr t½ in normal healthy adults is 14 to 50 seconds (23).

Mean LVEF was also markedly increased following treatment in the perhexiline group (by 9.9+2.0 absolute percentage points, a relative increase of 42%) and unchanged in the placebo group (p<0.001). Whilst left ventricular diastolic volume tended to decrease in the perhexiline group (p=0.06), systolic volume was significantly reduced (p<0.001) suggesting an increase in myocardial contractility. There was a significant reduction in E:EA ratio following treatment with perhexiline reflecting a reduction in left ventricular end diastolic pressure. In addition long-axis systolic function was increased in the perhexiline group reflecting an improvement in subendocardial function.

Within the ischemic cohort, there was no significant difference in heart rate at rest or during dobutamine stress in both groups. However, there was a significant 15% (p=0.04) increase in resting mean PSV in the perhexiline group following treatment. This increase reflects the increases seen in long-axis function and LVEF. During tissue Doppler stress echocardiography; there was a trend towards an increase in PSV at baseline (p=0.07) in the perhexiline group but a marked increase in peak dose PSV (24% p=0.03). At lower doses of dobutamine the myocardial velocities are inevitably lower; these low velocities are further diminished when measured off-line when compared to those obtained on-line by pulsed tissue Doppler. This is because they are derived from regional mean velocities rather than peak velocities. Though standard practice; this diminution will artificially appear to diminish the significance of the differences at low myocardial velocities. This explains the contrast between the seemingly small differences in baseline and low dose stress tissue Doppler parameters compared to the consistent and large increases in LVEF and online PSV of the lateral mitral annulus.

Figure 4:
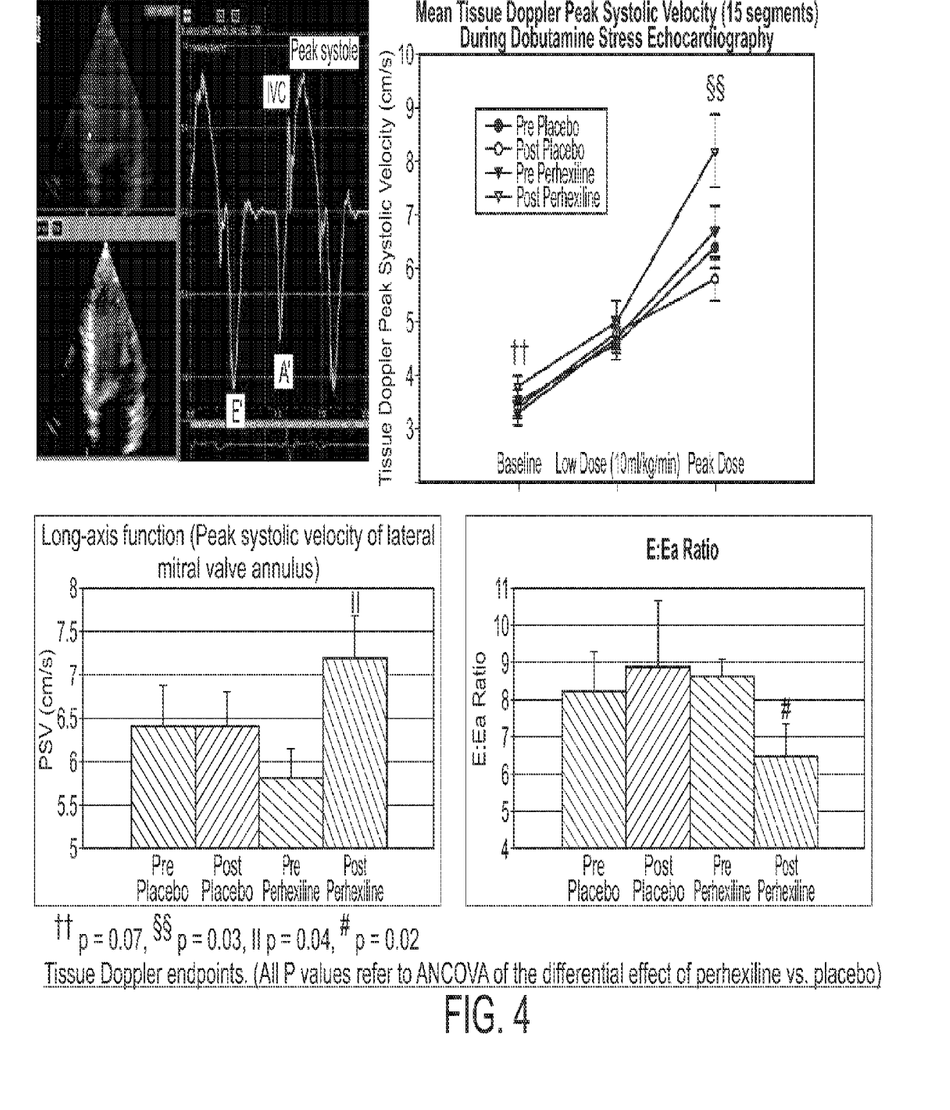
FIG. 4 shows data for primary and secondary end-points as discussed in the "Results" section.

The data for the primary and secondary end-points are depicted on FIGS. 3 and 4 and summarized on Table 2.

Discussion

As a result of these experiments, it was found that Perhexiline use resulted in significant improvements in peak exercise capacity, myocardial function at rest and stress, patient reported symptoms and skeletal muscle energetics. Remarkably; as well as being statistically highly significant, these improvements represent clinically significant improvements in patients who were already optimally treated. Our results suggest that perhexiline provides consistent improvements in these parameters, in the absence of significant side effects, irrespective of the initial inciting influence of CHF.

Without wishing to be bound by theory, the mechanism for the improvement seen in myocardial function with perhexiline is likely to be related to inhibition of FFA uptake and a metabolic shift towards the use of glucose and lactate. This may restores the failing hearts insulin sensitivity and makes it more oxygen efficient. In addition to requiring more oxygen than glucose to generate energy, excessive FFA metabolism has other potentially detrimental effects on the heart. FFA metabolism is known to uncouple oxidative phosphorylation and suppresses glucose oxidation through a direct inhibitory action on the glycolytic pathway. This inhibition causes increases lactate and proton accumulation within myocardial cells (Lopaschuk G O, Wambolt R B, Barr R L. "An imbalance between glycolysis and glucose oxidation is a possible explanation for the detrimental effects of high levels of fatty acids during aerobic reperfusion of ischemic hearts", J Pharmacal Exp Ther 1993; 264(1):135-144) leading to a fall in intracellular pH which is associated with a reduction in contractile function (Hausch G. "Hibernating myocardium", Physiol Rev 1998; 78(4):1055-1085). Furthermore, FFA metabolite accumulation have been shown to reduce ventricular arrhythmia threshold (Murnaghan M F. "Effect of fatty acids on the ventricular arrhythmia threshold in the isolated heart of the rabbit" Br J Pharmacal 1981; 73(4):909-915) and induce diastolic dysfunction (Depre C, Vanoverschelde J L, Taegtmeyer H. "Glucose for the heart", Circulation 1999; 99(4):578-588.).

The anti-anginal efficacy of perhexiline, both as mono- and combined therapy, is well documented (Horowitz J D, Mashford M L. "Perhexiline maleate in the treatment of severe angina pectoris", Med J Aust 1979; 1 (11):485-488; Cole P L, Beamer A D, McGowan N, Cantillon C O, Benfell K, Kelly R A et al. "Efficacy and safety of perhexiline maleate in refractory angina. A double-blind placebo-controlled clinical trial of a novel antianginal agent", Circulation 1990; 81(4):1260-1270). However, use of the drug declined due to reports of hepatotoxicity and peripheral neuropathy. It is now apparent that the risk of toxicity was related to the ability to metabolize the drug. 'Slow hydroxylators', with a genetic variant of the cytochrome P450-2D6, are particularly prone to progressive drug accumulation. In the absence of dosage adjustment; prolonged elevation of levels leads to phospholipid accumulation which may also occur with prolonged use of other CPT inhibitors, such as amiodarone. The risk of development of hepato-neuro-toxicity with perhexiline is markedly reduced by monitoring and maintaining serum levels between 0.15 and 0.60 mg/l. None of the patients in this study developed abnormal liver function tests or neuropathy as a consequence of perhexiline treatment followed by close serum level monitoring and titration.

$^{31}$P magnetic resonance spectroscopy was included in the study design to determine whether perhexiline treatment also improved skeletal muscle energetics. PCr t½ is a muscle bulk and workload independent marker of skeletal muscle mitochondrial function. The faster phosphocreatine recovery after exercise in the perhexiline treated patients suggested an improvement in skeletal muscle mitochondrial oxidative function. This may reflect an improvement in the heart failure syndrome and/or be a direct consequence of the metabolic substrate shift in skeletal muscle.

The results of the current study therefore establish that perhexiline exerts incremental benefits on symptomatic status, left ventricular function at rest and peak stress, and skeletal muscle metabolism in patients with stable chronic heart failure, over and above standard neurohumoral therapy. Indeed, the improvements in VO$_2$max were comparable to those seen in patients treated with beta-blockers (Hulsmann M, Sturm B, Pacher R, Berger R, Bojic A, Frey B et al. "Long-term effect of atenolol on ejection fraction, symptoms, and exercise variables in patients with advanced left ventricular dysfunction", J Heart Lung Transplant 2001; 20(11):1174-10 1180) but exceeded those seen with ACE inhibitors (Vescovo G, Dalla L L, Serafini F, Leprotti C, Facchin L, Volterrani M et al. <<Improved exercise tolerance after losartan and enalapril in heart failure: correlation with changes in skeletal muscle myosin heavy chain composition", Circulation 1998; 98(17):1742-1749), spironolactone (Cicoira M, Zanella L, Rossi A, Golia G, Franceschini L, Brighetti G et al. "Long-term, dose-dependent effects of spironolactone on left ventricular function and exercise tolerance in patients with chronic heart failure", J Am Coli Cardiel 2002; 40(2):304-310) or even with biventricular pacing (Auricchio A, Stellbrink C, Butter C, Sack S, Vogt J, Misier A R et al. "Clinical efficacy of cardiac resynchronization therapy using left ventricular pacing in heart failure patients stratified by severity of ventricular conduction delay", J Am Coli Cardiel 2003; 42(12):2109-2116). As this study included patients with and without significant coronary artery disease who all benefited, the benefit cannot therefore be ascribed purely to an anti-ischemic mechanism, rather, it is suggestive of our hypothesis that Perhexiline is modifying the central metabolic remodeling of CHF.

The contents of all references cited herein are hereby incorporated herein in their entirety for all purposes.

TABLE 1

Baseline characteristics and treatment

|  | Placebo Group | Perhexiline Group |
|---|---|---|
| N | 28 | 28 |
| Ischemic:Non Ischemic | 13:15 | 13:15 |
| Age | 63 ± 2 | 63 ± 2 |
| Sex (M:F) | 23:5 | 27:1 |
| Weight (kg) | 83 ± 3 | 89 ± 3 |
| Height (cm) | 165 ± 6 cm | 175 ± 2 cm |
| Body mass index | 28 ± 1 | 29 ± 1 |
| NYHA Class | | |
| Pre: | 2.2 ± 0.1 | 2.4 ± 0.1 |
| Post: | 2.1 ± 0.1 | 1.9 ± 0.2$^+$ |
| Corrected QT Interval | | |
| Pre: | 421 ± 7 ms | 413 ± 11 ms |
| Post: | 421 ± 9 ms | 413 ± 13 ms |
| Diabetes | 2 | 5 |
| Loop Diuretic | 20 | 17 |
| ACE Inhibitor | 25 | 22 |
| Lisinopril (mean dose) | 22 ± 4 mg | 23 ± 3 mg |
| Ramipril | 10 mg | 8.3 ± 1 mg |
| Perindopril | 6 mg | 6 mg |
| Enalapril | 22 ± 10 mg | 15 ± 5 mg |
| Trandolapril | 4 mg | 4 mg |
| AT2 Receptor Blockers | 4 | 3 |
| Losartan | 63 ± 38 mg | 100 mg |
| Vaisartan | 80 mg | 80 mg |
| Irbersartan | 175 ± 125 mg | ~ |
| Beta-Blockers | 15 | 18 |
| Carvedilol | 37 ± 10 mg | 50 mg |
| Bisoprolol | 2 ± 0.4 mg | 4 ± 1 mg |
| Metoprolol | 75 ± 25 mg | 100 mg |
| Atenolol | 67 ± 17 mg | 69 ± 19 mg |
| Aspirin | 15 | 11 |
| Clopidogrel | 1 | 3 |
| Warfarin | 9 | 9 |
| Calcium Channel Blockers | 5 | 3 |
| Spironolactone (mean dose) | 7 (21 ± 4 mg) | 6 (23 ± 2 mg) |
| Amiodarone | 4 | 1 |
| Oral Hypoglycaemics | 1 | 2 |
| Insulin | 0 | 2 |
| Statin | 18 | 12 |
| Serum perhexiline levels: | | |
| Week 1: | 0 | 0.57 ± 0.19 mg/l |
| Week 4: | 0 | 0.67 ± 0.20 mg/l |
| Week 8: | 0 | 0.43 ± 0.12 mg/l |

$^+$p = 0.02

TABLE 2

Primary and secondary endpoints. (All P values refer to AN CO VA of the differential effect of perhexiline vs. placebo)

|  | Placebo Group | Perhexiline Group | P value |
|---|---|---|---|
| VO$_2$max (ml/kg/min) | | | |
| Pre: | 16.3 ± 0.8 | 16.1 ± 0.6 | *<0.001 |
| Post: | 16.0 ± 0.9 | 18.8 ± 1.1* | |
| Exercise Time (mins) | | | |
| Pre: | 9.9 ± 1.2 | 10.5 ± 1.2 | |
| Post: | 10.9 ± 0.9 | 12.3 ± 1.1 | |

TABLE 2-continued

Primary and secondary endpoints. (All P values refer to AN CO VA of the differential effect of perhexiline vs. placebo)

| | | | Placebo Group | Perhexiline Group | P value |
|---|---|---|---|---|---|
| Respiratory exchange ratio during peak exercise[+] | | | | | |
| Pre: | | | 1.1 ± 0.02 | 1.1 ± 0.03 | |
| Post: | | | 1.1 ± 0.02 | 1.1 ± 0.03 | |
| Resting BP (mmHg) | | | | | |
| Pre: | | | 111/63 ± 5/3 | 116/69 ± 7/4 | |
| Post: | | | 113/67 ± 5/4 | 113/67 ± 7/4 | |
| Peak Exercise BP (mmHg) | | | | | |
| Pre: | | | 141/69 ± 5/4 | 141/75 ± 9/3 | |
| Post: | | | 137/68 ± 7/4 | 142/70 ± 9/5 | |
| Resting Heart Rate($min^{-1}$) | | | | | |
| Pre: | | | 76 ± 4 | 73 ± 3 | |
| Post: | | | 78 ± 4 | 73 ± 3 | |
| Peak Exercise Heart Rate($min^{-1}$) | | | | | |
| Pre: | | | 124 ± 6 | 121 ± 6 | |
| Post: | | | 121 ± 5 | 120 ± 5 | |
| Minnesota living with heart failure questionnaire score | | | | | |
| Pre: | | | 42 ± 5 | 45 ± 5 | |
| Post: | | | 40 ± 4 | 34 ± 5[†] | [†]0.04 |
| Left ventricular end-diastolic volume (ml) | | | | | |
| Pre: | | | 213 ± 16 | 232 ± 11 | |
| Post: | | | 216 ± 16 | 212 ± 9 | |
| Left ventricular end-systolic volume (ml) | | | | | |
| Pre: | | | 159 ± 13 | 176 ± 8 | [‡]<0.001 |
| Post: | | | 162 ± 14 | 140 ± 8[‡] | |
| Left ventricular ejection fraction (%) | | | | | |
| Pre: | | | 26 ± 1 | 24 ± 1 | [§]<0.001 |
| Post | | | 26 ± 1 | 34 ± 2[§] | |
| Long axis function (cm/s) | | | | | |
| Pre: | | | 6.4 ± 0.6 | 5.8 ± 0.4 | [∥]0.04 |
| Post: | | | 6.4 ± 0.5 | 7.2 ± 0.6[∥] | |
| E:EA Ratio | | | | | |
| Pre: | | | 8.3 ± 1.0 | 8.6 ± 0.6 | [#]0.02 |
| Post: | | | 8.9 ± 1.8 | 6.5 ± 0.9[#] | |
| PCr t½ (seconds) | | | | | |
| Pre: | | | 58 ± 10 | 67 ± 15 | [**]<0.05 |
| Post: | | | 73 ± 24 | 44 ± 7[**] | |
| Dobutamine Stress Echocardiography: | | | | | |
| Heart Rate: | Rest | Pre | 67 ± 5 | 57 ± 2 | |
| | | Post | 66 ± 6 | 53 ± 2 | |
| | Low Dose | Pre | 86 ± 8 | 78 ± 7 | |
| | | Post | 74 ± 6 | 65 ± 6 | |
| | Peak Dose | Pre | 130 ± 5 | 126 ± 4 | |
| | | Post | 128 ± 5 | 122 ± 3 | |
| Mean PSV (15 segments) | Rest | Pre | 3.5 ± 0.2 | 3.3 ± 0.2 | [††]0.07 |
| | | Post | 3.4 ± 0.2 | 3.8 ± 0.2[††] | |
| | Low Dose | Pre | 4.6 ± 0.3 | 4.7 ± 0.3 | |
| | | Post | 4.8 ± 0.3 | 5.0 ± 0.5 | |
| | Peak Dose | Pre | 6.4 ± 0.4 | 6.6 ± 0.5 | |
| | | Post | 5.8 ± 0.4 | 8.2 ± 0.8[§§] | [§§]0.003 |

[+]Ratio of $CO_2$ emission/oxygen consumption

What is claimed is:

1. A method for treating chronic heart failure or a symptomatic component/feature/condition thereof in a mammal, comprising:
   diagnosing the mammal as having chronic heart failure or a symptomatic component/feature/condition thereof; and
   administering to said mammal a therapeutically-effective amount of perhexiline.

2. The method of claim 1, wherein the therapeutically-effective amount of perhexiline is sufficient to reduce or ameliorate the chronic heart failure or a symptomatic component/feature/condition thereof in the mammal.

3. The method of claim 2, wherein the perhexiline is in the form of a maleate salt.

4. The method of claim 1, wherein the perhexiline is in the form of a pharmaceutically acceptable salt.

5. The method of claim 1, wherein the mammal is a human.

6. The method of claim 1, further comprising co-administering to said mammal at least one therapeutic compound.

7. The method of claim 6, wherein the therapeutic compound is selected from a member of the group consisting of Alpha Blockers, Beta Blockers, Calcium Channel Blockers, Diuretics, Ace (Angiotensin-Converting Enzyme) Inhibitors, Arb (Angiotensin II Receptor Blockers), Spironolactone, Nitrate, Warfarin, Verapamil, Insulin, Amiodarone, Lisinopril, Ramipril, Perindopril, Enalapril, Trandolapril, At2 Receptor Blockers, Losartan, Valsartan, Irbersartan, Carvedilol, Bisoprolol, Metoprolol, Atenolol, Aspirin, Clopidogrel, Oral Hypoglycaemics, Disopyramide, and Statins.

8. The method of claim 1, further comprising co-administering to said mammal at least one therapeutic compound advantageous in treating chronic heart failure or a symptomatic component/feature/condition thereof.

9. The method of claim 1, wherein the symptomatic component/feature/condition is member of the group consisting of dyspnoea (shortness of breath), chest pain, fatigue, palpitation, and syncope.

10. The method of claim 9, further comprising:
   determining a NYHA classification score (breathlessness) of the mammal before and after administration of perhexline, wherein a decreased NYHA score after administration of perhexline indicates a reduction in the extent of chronic heart failure or a symptomatic component/feature/condition thereof in the mammal.

11. The method of claim 10, wherein the NYHA classification score of the mammal after administration of perhexline decreases from Class III to Class II.

12. The method of claim 1, wherein the symptomatic component/feature/condition is member of the group consisting of reduced left ventricular ejection fraction (LVEF), reduced E:EA ratio, abnormally rapid skeletal muscle phosphocreatine depletion with delayed recovery, reduced systolic velocity (PSV), diminished exercise capacity or tolerance, diminished peak oxygen consumption (VO2max) during exercise, and impaired myocardial energetic state (PCr/γATP ratio).

13. The method of claim 1, wherein the extent of chronic heart failure in the mammal is diagnosed in accordance with the New York Heart Association (NYHA) diagnostic system.

14. The method of claim 1, wherein the extent of chronic heart failure in the mammal is diagnosed in accordance with the Minnesota Living with Heart Failure Questionnaire (ML-HFQ) scoring system.

15. The method of claim 14, further comprising
   determining a MLHFQ (quality of life) score of the mammal before and after administration of perhexline, wherein a decreased MLHFQ score after administration of perhexline indicates a reduction in the extent of chronic heart failure or a symptomatic component/feature/condition thereof in the mammal.

16. The method of claim 1, further comprising
   determining peak oxygen consumption (VO2max) in the mammal during exercise wherein an increase in peak oxygen consumption (VO2max) in the mammal after administration of perhexline indicates a reduction in the extent of chronic heart failure or a symptomatic component/feature/condition thereof in the animal.

17. The method of claim 1, wherein perhexiline is administered in an amount of 300 mg per day or less.

18. The method of claim 1, wherein perhexiline is administered in an amount of 100 mg per day or less.

19. The method of claim 1, wherein perhexiline is administered in an amount of 100 mg to 300 mg per day.

20. The method of claim 1, wherein the chronic heart failure or a symptomatic component/feature/condition thereof in a mammal is due to or associated with a member of the group consisting of: ischaemia, coronary artery disease, cardiomyopathy, hypertension, diabetes, and valvular disease.

21. The method of claim 1, further comprising: monitoring and maintaining serum levels of perhexiline in said mammal in a range of about 0.15 and about 0.60 mg/l.

\* \* \* \* \*